US009409776B2

(12) United States Patent
Day et al.

(10) Patent No.: US 9,409,776 B2
(45) Date of Patent: *Aug. 9, 2016

(54) STRONTIUM PHOSPHATE MICROPARTICLE FOR RADIOLOGICAL IMAGING AND THERAPY

(71) Applicant: MO-SCI Corporation, Rolla, MO (US)

(72) Inventors: Delbert E. Day, Rolla, MO (US); Yiyong He, Rolla, MO (US)

(73) Assignee: MO-SCI Corporation, Rolla, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 14/519,587

(22) Filed: Oct. 21, 2014

(65) Prior Publication Data

US 2015/0118139 A1    Apr. 30, 2015

Related U.S. Application Data

(63) Continuation of application No. 12/883,827, filed on Sep. 16, 2010, now Pat. No. 8,865,123.

(51) Int. Cl.
| *A61K 51/02* | (2006.01) |
| *A61K 51/12* | (2006.01) |
| *C01B 25/45* | (2006.01) |
| *C01B 25/32* | (2006.01) |

(52) U.S. Cl.
CPC ............... *C01B 25/45* (2013.01); *A61K 51/02* (2013.01); *A61K 51/1251* (2013.01); *C01B 25/32* (2013.01); *C01P 2004/60* (2013.01); *C01P 2004/61* (2013.01); *C01P 2006/12* (2013.01); *C01P 2006/44* (2013.01); *Y10T 428/2982* (2015.01)

(58) Field of Classification Search
CPC . A61K 51/025; A61K 51/02; A61K 51/1251; C01B 25/32; C01B 25/45; Y10T 428/2982; C01P 2006/44; C01P 2004/60; C01P 2004/61; C01P 2006/12
See application file for complete search history.

(56) References Cited

U.S. PATENT DOCUMENTS

| 3,331,784 A | 7/1967 | Meyer et al. |
| 3,851,044 A | 11/1974 | Adler et al. |
| 4,339,421 A | 7/1982 | Schultess et al. |
| 4,789,501 A | 12/1988 | Day et al. |
| 5,011,677 A | 4/1991 | Day et al. |
| 5,011,797 A | 4/1991 | Day et al. |
| 5,302,369 A | 4/1994 | Day et al. |
| 5,560,901 A | 10/1996 | Brodack et al. |
| 5,611,833 A | 3/1997 | Brahmbhatt et al. |
| 5,651,956 A | 7/1997 | Nosco et al. |
| 5,690,908 A | 11/1997 | Deutsch et al. |
| 6,165,440 A | 12/2000 | Esenaliev |
| 6,358,531 B1 * | 3/2002 | Day et al. ............ 424/489 |
| 6,379,648 B1 | 4/2002 | Day et al. |
| 6,455,024 B1 | 9/2002 | Glajch et al. |
| 6,537,518 B1 | 3/2003 | Gray |
| 6,589,549 B2 | 7/2003 | Shih et al. |
| 6,797,704 B2 | 9/2004 | Leong et al. |
| 7,534,448 B2 | 5/2009 | Saltzman et al. |
| 7,768,399 B2 | 8/2010 | Hachmann et al. |
| 7,959,900 B2 * | 6/2011 | Peng et al. .......... 424/1.11 |
| 8,865,123 B1 * | 10/2014 | Day et al. .......... 424/1.61 |
| 2004/0197264 A1 | 10/2004 | Schwarz et al. |
| 2004/0258614 A1 | 12/2004 | Line et al. |
| 2007/0053830 A1 | 3/2007 | Peng et al. |
| 2008/0038190 A1 | 2/2008 | Simpson et al. |
| 2008/0226547 A1 | 9/2008 | Larsen et al. |
| 2009/0208428 A1 | 8/2009 | Hill et al. |
| 2010/0055019 A1 | 3/2010 | Day et al. |
| 2010/0160527 A1 | 6/2010 | Royer et al. |

FOREIGN PATENT DOCUMENTS

| CN | 1127093 A | 12/1999 |
| CN | 1640498 A | 7/2005 |
| CN | 101284161 A | 10/2008 |
| CN | 101321542 A | 12/2008 |
| EP | 1162626 A1 | 12/2001 |
| WO | 0029034 | 5/2000 |
| WO | 2005087274 | 9/2005 |
| WO | 2005/993673 A2 | 10/2005 |
| WO | 2009/064460 A2 | 5/2009 |

OTHER PUBLICATIONS

Conzone, S. et al., Journal of Biomedical Materials Research, Part A (2008), 88A, (2), 531-542.*
International Search Report, PCT/US2014/061597, dated Jun. 25, 2015, 5 pages.
Written Opinion, PCT/US2014/061597, dated Jun. 25, 2015, 6 pages.
Sinouh et al., "Effect of TiO2 and SrO additions on some physical properties of 33Na2O-xSrO-xTiO2-(50-2x)B2O3-17P2O5 glasses", Journal of Thermal Analysis and Calorimetry, 2013, vol. 111, No. 1, pp. 401-408.
Yao, et al., "In vitro Bioactive Characteristics of Borate-based Glasses with Controllable Degradation Behavior," 2007, Journal of the American Ceramic Society.
Cast Steel: Gas Nitriding, Keyto Metals, 2009-2010. (not attributed).
Turker and Ozer, Diagnostic Radiopharmaceutical Agents, Journal of Pharmaceutical Science, 29, 145-154, 2004.
Karesh, et al., Radiopharmaceuticals in Nuclear Medicine, nucmedtutorials.com, Apr. 8, 2010.
Saatchi and Hafeli, Radiolabeling of Biodegradable Polymeric Microspheres with [99mTc(C0)3]+ and in Vivo Biodistribution Evaluation using MicroSPECT/CT Imaging, Bioconjugate Chem., 2009, 20, 1209-1217.
Christoffersen, et al., "Effects of Strontium Ions on Growth and Dissolution of Hydroxyapatite and on Bone Mineral Detection," Bone, Official Journal of the International Bone and Mineral Society, vol. 20, Issue 1, pp. 47-54, Jan. 1997.

(Continued)

*Primary Examiner* — Michael G Hartley
*Assistant Examiner* — Leah Schlientz
(74) *Attorney, Agent, or Firm* — Senniger Powers LLP

(57) ABSTRACT

This invention relates to a method for making strontium-phosphate microparticles that incorporate radioisotopes for radiation therapy and imaging.

17 Claims, No Drawings

(56) References Cited

OTHER PUBLICATIONS

Dedhiya, et al., "Mechanism for the Retardation of the Acid Dissolution Rate of Hydroxyapatite by Strontium," Journal of Dental Research, 1973; 52; 1097.

Pan, et al., "Strontium Borate Glass: Potential Biomaterial for Bone Regeneration," Journal of the Royal Society; doI: 10.1098/rsif.2009. 0504; Dec. 23, 2009.

Wu, "The Study of Strontium Niobium Phosphate Glass Properties and Structure," Master's Thesis, date of defense Jul. 7, 2009.

Sudarsanan and Young, "Structure of Strontium Hydroxide Phosphate, $Sr_5(PO_4)_3OH$," Act Cryst. (1972), B28, 3668.

Abstract of JP 09-165327.

Abtract of JP 09-165328.

\* cited by examiner

STRONTIUM PHOSPHATE MICROPARTICLE FOR RADIOLOGICAL IMAGING AND THERAPY

REFERENCE TO RELATED APPLICATIONS

This application is a continuation of application Ser. No. 12/883,827 filed Sep. 16, 2010 and issued Oct. 21, 2014 as U.S. Pat. No. 8,865,123, the entire disclosure of which is expressly incorporated herein by reference.

FIELD OF THE INVENTION

The field of the present invention is radiomicroparticles for medical therapy and imaging, and particularly radioactive strontium phosphate microparticles for radiological imaging and radioisotope therapy.

BACKGROUND

In the treatment of patients with certain kinds of cancer or rheumatoid arthritis, methods are known in which radioactive particles are introduced intravascularly to a tumor site (radioembolism) or locally into the synovial fluid in a joint in order to trap the radioactive particle at a particular site for its radiation effect. Similar methods are used for imaging parts of the body, organs, tumors, and so forth.

According to this technique, a quantity of the radioactive particles are injected into a localized area of the patient to be imaged and/or treated. For imaging, gamma emitting materials are commonly used to label carriers that provide imaging of a tissue area, tumor or organ. Some of these carriers have a specific affinity for certain binding sites or biochemical targets allowing target specific or location specific uptake of the labelled carrier.

Radiological imaging of various tissues in the human body is commonly accomplished using Technetium-99m. $^{99m}$-TC is a well-known radioactive isotope used for radiodiagnostics. It emits detectable low level 140 keV gamma rays, has a half-life of 6 hours and decays to Tc-99 in 24 hours (93.7%). It is used for imaging and function studies of the brain, myocardium, thyroid, lungs, liver, gallbladder, kidneys, bone, blood, and tumors. It is reported to be used in over 20 million diagnostic nuclear medicine procedures each year.

Targeted radiation therapy using microparticles or microspheres is also a well-developed field radioisotope therapy. Radionuclides such as Yttrium-90 and Holmium-166 are commonly used radioactive beta emitters in microsphere radiotherapy. Polymer microspheres such as albumin, polylactic acid derivatives, and so forth, and glass microspheres, are both generally known in the medical arts for use in delivering both pharmaceuticals and radiopharmaceuticals to specific tissue sites.

However, a need remains for a radioactive microparticle for delivery of one or more radiopharmaceuticals and which have characteristics which will permit the microparticles to be suitable for injection into a patient for localized imaging or therapy.

BRIEF SUMMARY OF THE INVENTION

In a preferred embodiment there is provided a strontium phosphate radiomicroparticle, made by the process comprising:

reacting a strontium-containing borate glass microparticle with a phosphate solution of a sufficient concentration and for a sufficient time under suitable conditions to convert the strontium-containing borate glass microparticle to a strontium phosphate microparticle; and bonding at least one radioisotope suitable for radioimaging and/or radiotherapy to said strontium phosphate microparticle.

In other preferred embodiments, there are provided additional features available singularly and in combination.

In one preferred process, there is provided wherein the strontium-containing borate glass microparticle is a microsphere having a diameter of about 20 μm to about 50 μm.

In one preferred process, there is provided wherein the strontium phosphate microparticle has a surface area of between about 90 to about 200 square meters per gram. In one preferred process, there is provided wherein the at least one radioisotope is a therapeutic beta-emitting radioisotope; and/or wherein the at least one radioisotope is a diagnostic gamma-emitting radioisotope; and/or wherein the at least one radioisotope is a combination of a therapeutic beta-emitting radioisotope and a diagnostic gamma-emitting radioisotope.

In one preferred process, there is provided wherein the step of bonding said at least one radioisotope suitable for radioimaging and/or radiotherapy to the strontium phosphate microparticle is prepared in situ in a clinical setting by mixing just prior to the time of administration to a patient said strontium phosphate microparticle with the at least one radioisotope suitable for radioimaging and/or radiotherapy.

In one preferred process, there is provided wherein the at least one radioisotope is Technetium-99m; and/or wherein the at least one radioisotope is selected from the group consisting essentially of Technetium-99m, Indium-111, Lutetium-177, Sarnarium-153, Yttrium-90, and mixtures thereof.

In another preferred embodiment, there is provided a strontium phosphate radiomicropa 1iide made according to the process described herein.

In one preferred radiomicroparticle, there is provided wherein the at least one radioisotope comprises at least two different radiosotopes; and/or wherein the at least one radioisotope comprises at least three different radioisotopes.

In another preferred embodiment, there is provided a method of administering strontium-phosphate radiomicroparticles to a patient in need thereof, comprising locally delivering by catheter or suitable intravenous injection to a tissue target or organ of the patient a composition comprising strontium-phosphate microparticles with at least one radioisotope bonded thereto and a physiologically acceptable carrier.

In other preferred methods, there are provided additional features available singularly and in combination.

In one preferred method, there is provided wherein the at least one radioisotope is a radiodiagnostic agent; and/or wherein the at least one radioisotope is a radiotherapeutic agent;

and/or wherein the at least one radioisotope comprises a radiodiagnostic agent and a radiotherapeutic agent.

In one preferred method, there is provided wherein the at least one radioisotope comprises at least two different radiosotopes; and/or wherein the at least one radioisotope comprises at least three different radioisotopes.

In one preferred method, there is provided wherein the at least one radioisotope is technetium-99m; and/or wherein the at least one radioisotope is selected from the group consisting essentially of Technetium-99m, Indium-111, Yttrium-90, Lutetium-177, Samarium-153, and mixtures thereof; and/or wherein the composition also contains an additional radiotherapeutic agent.

In one preferred method, there is provided wherein the tissue target or organ is selected from the group consisting of: brain, myocardium, thyroid, lung, liver, spleen, gallbladder, kidney, bone, blood, and head and neck tumor, prostate, breast, and uterine, In one preferred method, there is provided wherein the strontium phosphate microparticles with at least one radioisotope are prepared in situ in a clinical setting by mixing just prior to the time of administration to a patient said strontium phosphate microparticle with the at least one radioisotope suitable for radioimaging and/or radiotherapy.

In another preferred embodiment, there is provided a method of obtaining a radiologic image of a specific tissue or organ of a patient, comprising administering by catheter or suitable intravenous injection to a tissue target or organ of the patient a composition containing strontium-phosphate microparticles with at least one radiodiagnostic agent bonded thereto in a physiologically acceptable carrier, and obtaining the radiologic image of the specific tissue or organ of the patient by capturing the gamma radiation emitted by the radiodiagnostic agent using a suitable radionuclide imaging technique.

Additional features of this method include: wherein the at least one radioisotope is a radiodiagnostic agent; wherein the radiodiagnostic agent is Technetium-99m; and wherein the tissue target or organ is selected from the group consisting of: brain, myocardium, thyroid, lung, liver, spleen, gallbladder, kidney, bone, blood, and head and neck tumor, prostate, breast, and uterine.

In other preferred embodiments, there are provided additional features available singularly and in combination, including: wherein the strontium-containing borate glass microparticle is fully converted to a strontium phosphate microparticle through to the interior, or wherein it is partially converted to create a porous layer over an unconverted glass core; wherein the strontium-containing borate glass microparticle is between about 20 and about 40 microns in diameter; wherein the strontium phosphate microparticle is amorphous or crystalline; wherein the strontium phosphate microsphere is porous; and wherein the strontium-containing borate glass microsphere is fully converted to a strontium phosphate microparticle. In some embodiments, the strontium-containing borate glass microparticle may be substantially calcium-free.

In another preferred embodiment, the at least one radioisotope is any approved radiopharmaceutical available to nuclear medicine practitioners.

In a further preferred embodiment, the method further comprises wherein the radionuclide imaging technique is single photon emission computed tomography (SPECT).

DETAILED DESCRIPTION OF THE INVENTION

In accordance with the present invention, novel porous strontium phosphate microparticle carriers have been devised for use in the imaging and/or treatment of certain cancers, tumor bearing tissue, rheumatoid arthritis, or other diseases where nuclear medicine imaging or treatment is indicated. These carriers constitute microparticles that comprise a porous strontium-phosphate material having one or more radiopharmaceuticals bound to the surface. Both radiodiagnostic gamma emitting agents and radiotherapeutic beta emitting agents are contemplated.

Overview

The strontium phosphate radiomicroparticle of the present invention is made by reacting a strontium-containing borate glass microparticle with a phosphate solution in amounts and for a sufficient time under suitable conditions to convert the strontium-containing borate glass microparticle to a strontium phosphate microparticle, and bonding at least one radioisotope suitable for radioimaging and/or radiotherapy in a mammal to said strontium phosphate microparticle.

The phosphate solution conversion process converts a solid strontium borate glass into a porous strontium phosphate material. By manufacturing a non-radioactive solid strontium-containing borate glass microparticle of a specific diameter, the conversion results in a porous strontium phosphate microparticle of a specific diameter. Due to the substantially thorough chemical action of the phosphate solution on the borate glass, a substantially pure porous strontium phosphate material having a high surface area is achieved in the location where the phosphate solution has reacted with the borate glass.

The porosity of the resulting strontium phosphate material and the controllable size and number of the microparticles provide an excellent delivery platform for delivering compounds of interest to specific locations. Thus, the process of manufacturing of the microsphere has been divorced from the process of adding the radiolabel or radiotherapeutic. This provides nuclear medicine professionals the ability to control the radiodiagnostic and radiotherapeutic regimen by allowing, in the clinical setting, at or near the time of delivery, the decision of the type and quantity of radiopharmaceutical(s) to be incorporated into the delivery vehicle.

Advantages

Some of the advantages provided by this approach include: the ability to adsorb a radioisotope or combination of radioisotopes onto a porous microparticle, the ability to customize dose to the patient, customize imaging of the tissue, reducing time-related degradation of the activated radiopharmaceutical, and reducing exposure to medical personnel.

An additional advantage provided by this approach includes an increase in radio-opacity which provides clearer radiographic images due to the use of strontium phosphate rather than calcium apatite.

A further advantage provided by this approach includes the ability to blend two or more different radioisotopes. Further, this allows for the therapy to be able to change over time, or be customized to a particular set of circumstances.

A further advantage is the ability to use radioisotopes that have a short half-life and to avoid using microparticle manufacturing processes that would vaporize certain radioisotopes such as Technetium and Rhenium.

Porosity

Importantly, the strontium phosphate microparticles achieve a porosity, or surface area, that allows for a significant amount of radioisotope to be bound. It is contemplated that surface area values of 90 to 200 square meters per gram are within the scope of the present invention. Significantly, prior art attempts using calcium apatite to create the microparticles have provided much lower surface area values of only 40 sq. meters per gram, or less.

Further, these calcium-only microparticles demand complex manufacturing that includes a two-step process to adsorb the isotope requiring a binder, a heating step that destroys the surface area, and chemical precipitation.

These radioactive substantially spherical strontium phosphate radiomicroparticles are made by reacting a pre-made strontium-containing borate glass microparticle with a phosphate solution in amounts and for a sufficient time under suitable conditions to convert, partially or fully, the strontium-containing borate glass microparticle to an amorphous or crystalline strontium phosphate microparticle. Once the glass has been converted and the porous material is made, a radioisotope-bearing radiopharmaceutical is then adsorbed or bonded to the substantially pure strontium phosphate microparticle and is then suitable for radioimaging and/or radiotherapy in a mammal.

Phosphate Conversion

The phosphate solution conversion process converts a solid strontium borate glass microparticle into a porous strontium phosphate material that can be either amorphous or crystalline. The glass can be converted completely thus forming a completely porous or even hollow microparticle. The glass can also be partially converted thus resulting in a glass core surrounded by a porous strontium phosphate layer. The conversion of the borate glass is performed by exposing it to an aqueous phosphate solution. Many different phosphate solutions are contemplated as within the scope of the present invention. One non-limiting example includes phosphate buffered saline (PBS). PBS may be prepared in many different ways. Some formulations do not contain potassium, while others contain calcium or magnesium. Generally, PBS contains the following constituents: 137 mM NaCl, 2.7 mM KCl, 10 mM sodium phosphate dibasic, 2 mM potassium phosphate monobasic and a pH of 7.4. Another non-limiting example is a 0.25 M K2PO$_4$ solution. Non-saline phosphate solutions may be prepared using monosodium phosphate (NaH2PO$_4$), disodium phosphate (Na2HPO$_4$), and water, with phosphoric acid or sodium hydroxide to adjust the pH as desired.

Other concentrations and types of aqueous phosphate solutions are contemplated as within the scope of the invention.

Strontium

Conversion of the strontium borate glass results, at the molecular level, in a high surface-area porous material, that itself, is an agglomeration containing the strontium phosphate compound. The pores of the surface provide access to the strontium phosphate compound. When a radioisotope is mixed with the microparticles, a strong chemical bond is made with the exposed strontium phosphate compound. Without being held to any particular chemical reaction or theory, it is believed that the isotope can bind in a substitution reaction removing a phosphate [PQ4 group], or it may be bound into a void space or it may substitute for a strontium ion [Sr+$^2$].

Microparticle Size and Shape

By manufacturing a non-radioactive solid strontium-containing borate glass microparticle of a specific diameter, the conversion results in a porous strontium phosphate microparticle of a specific diameter. Since the starting material is a solid strontium-containing borate glass microparticle and it becomes fully (or partially) converted to a porous strontium phosphate microparticle, the physical parameters of shape, size, diameter are dictated by the glass microparticle manufacturing process. Importantly, the size and dimension of the converted strontium microparticle are substantially the same as the size and dimension of the starting strontium borate glass microparticle. This feature provides the significant advantage of being able to control the size and dimension of the delivery vehicle itself, the porous strontium phosphate microparticle.

"Microparticle", as used herein, generally refers to a particle of a relatively small size, but not necessarily in the micron size range; the term is used in reference to particles of sizes that can be less than 50 nm to 1000 microns or greater. "Radiomicroparticle" refers to the microparticles of the present invention with one or more radioisotopes adsorbed thereon. The microparticles are preferably round spheroids having a preferred diameter of about 20 μm and above. In other preferred embodiments, the microparticles range from about 20 μm to about 200 μm, from about 30-80 μm, from about 20-40 μm, and from about 25 μm to 38 μm. In another embodiment, the diameter of the particles is from about 5 to about 100 microns, preferably from about 10 to about 50 microns. As used herein, the microparticle encompasses microspheres, microcapsules, ellipsoids, fibers, and microparticles, unless specified otherwise.

Customized Delivery

The porosity of the resulting strontium phosphate material and the controllable size and number of the microparticles provide an excellent delivery platform for delivering radiation to specific locations.

Importantly, no radioisotope is incorporated in the borate glass microparticle.

Thus, the process of manufacturing of the microsphere has been divorced from the process of adding the radioisotope label or the radiotherapeutic. Prior radiomicrospheres must be manufactured as glass or biopolymer particles with the radioisotope as a homogeneous integral component of the glass or biopolymer. The present inventive approach provides a medical radiology professional the ability to control the radiodiagnostic and radiotherapeutic regimen by allowing them, in the clinical setting, to decide the type and quantity of radiopharmaceutical(s) to incorporate into the delivery vehicle. Some of the advantages of this approach include the ability to customize the dose to the patient, customize imaging of the tissue, reducing time-related degradation of the activated radiopharmaceutical, and reducing exposure to medical personnel.

Delivery of Multiple Isotopes

Importantly, the combination of the significantly increased surface area and the electrical attraction of the radioisotope to the porous microparticle provides for bonding multiple radioisotopes to the microparticle. In preferred embodiments, two radiosisotopes are bound. Binding a first isotope to the porous microparticle is performed using simple mixing in an appropriate solution over a pre-determined time, and then washing and eluting out the unbound isotope. This provides a composition where a radioisotope is bound to the microparticles.

Binding a second isotope to the porous microparticle is performed by simple mixing in a solution having the second isotope. Importantly, the second isotope does not displace the first isotope since the microparticles have a large surface area, and a nuclear pharmacist or other professional can take advantage of the different binding capacities of various radioisotopes to the microparticles. Thus, three and even four different radioisotopes can be bound within a single dose, or batch, of microparticles.

Further, by using radiation dosimeters which show the keV peaks of various radioisotopes, activity can be tested, and tailored to a specific therapy. For example, treatment could in one non-limiting example consist of 100 units of isotope #1 and 50 units of isotope #2.

Delivery to Tissue

The microparticles may be administered to the patient through the use of catheters either alone or in combination with vasoconstricting agents or by any other means of administration that effectively causes the microparticles to become embedded in the cancerous or tumor bearing tissue. For purposes of administration, the microparticles are preferably suspended in a medium that has a sufficient density or viscosity that prevents the microparticles from settling out of suspension during the administration procedure. Presently preferred liquid vehicles for suspension of the microparticles include polyvinylpyrrolidone (PVP), sold under the trade designation Plasdone K-30 and Povidone by GAF Corp, a contrast media sold under the trade designation Metrizamide by Nyegard & Co. of Oslo, Norway, a contrast media sold under the trade designation Renografin 76 by E. R. Squibb & Co., 50% dextrose solutions and saline.

Types of Radioisotopes

In a preferred embodiment of the present invention, the radioisotopes/radionuclides are chosen so that when administered to the patient, the microparticles may emit either beta radiation, gamma radiation, or both. The beta emitter is chosen to deliver a therapeutic intensity and therapeutic amount of short-range (e.g., a penetration of the tissue on the order of about several millimeters or less) beta radiation but does not emit a significant amount of unwanted beta radiation which could have a negative impact on healthy tissue surrounding the cancerous or tumor bearing tissue. The gamma emitter is chosen to deliver a diagnostic intensity and diagnostic amount of longer-range (e.g., capable of external detection) gamma radiation but does not emit a significant amount of unwanted gamma radiation.

Since the radioisotopes/radionuclides may be bonded or prepared in situ just prior to delivery by a radiology professional, the type of radioisotope(s) may be chosen based on each patient's needs and diagnosis. By providing a patient-specific dosing, patient outcome is improved and side-effects are minimized. Patient data such as age, gender, weight, and pre-existing conditions are considered when determining a radiotherapeutic and/or radiodiagnostic profile. Cancer data such as tumor size, tumor type, tumor location, degree of surgical intervention and success, vascular structures within and adjacent to the area being treated, and organ involvement are also considered when determining a radiotherapeutic and/or radiodiagnostic profile.

The radioisotope Yttrium-90 which form radioisotopes having a half-life greater than about two days and less than about 30 days is one particularly preferred therapeutic radioisotope which emit therapeutic beta radiation.

For radioimaging, the radioisotope technetium-99m is particularly preferred. [para 70] The present invention includes wherein the radioisotope is radiopharmaceutical grade and is selected from the group consisting essentially of, but not limited to: Actinium-225, Antimony-127, Arsenic-74, Barium-140, Bismuth-2 I0, Californium-246, Calcium-46, Calcium-47, Carbon-11, Carbon-14, Cesium-131, Cesium-137, Chromium-51, Cobalt-57, Cobalt-58, Cobalt-60, Dysprosium-165, Erbium-169, Fluorine-18, Gallium-67, Gallium-68, Gold-198, Hydrogen-3, Indium-111, Indium-113m, Iodine-123, Iodine-125, Iodine-131 Diagnostic, Iodine-131 Therapeutic, Iridium-192, Iron-59, Iron-82, Krypton-8 m, Lanthanum-140, Lutetium-177, Molybdenum-99, Nitrogen-13, Oxygen-15, Paladium-103, Phosphorus-32, Radon-222, Radium-224, Rhenium-186, Rhenium-188, Rb-82, Samarium-153, Selenium-75, Sodium-22, Sodium-24, Strontium-89, Technetium-99m, Thallium-201, Xenon-127, Xenon-133, Yttrium-90, and combinations, and mixtures thereof Where combinations of radioisotopes are used with the microparticles, preferred combinations of radioisotopes include having one or more beta emitters along with one or more gamma emitters. Examples include but are not limited to Y-90/In-111 Y-90/Tc-99m, P-32/In-111, P-32/Tc-99m, Ho-166/In-111, Ho-166/Tc-99m, Sm-153/In-111, and Sm-153/Tc-99m.

Particularly preferred radioisotopes include Tedmetium-99m and Indium-111 (radiodiagnostic gamma emitters), Lutetium-177 (being both a beta and gamma emitter), and Samarium-153 and Yttrium-90 (radiotherapeutic beta emitters), Tc-99m has been used for imaging and function studies of the brain, myocardium, thyroid, lungs, liver, gallbladder, kidneys, bone, blood, and tumors. Indium-111 pentetreotide has been used in imaging of neuroendocrine tumors that overexpress somatostatin receptors and has become standard for localization of these tumors. This radioligand is internalized into the cell and can induce receptor-specific cytotoxicity by emission of Auger electrons. Lutetium-177 having both gamma and beta properties enables its use in imaging as well as treatment. It has a shorter radius of penetration that Y-90 which makes it an ideal candidate for radiotherapy of small tumors. Samarium-153 lexidronam (chemical name Samarium-153-ethylene diamine tetrametbylene phosphonate, abbreviated Samariurn-153 EDTMP, trade narne Quadramet) is a complex of a radioisotope of the lanthanide element samarium with the chelator EDTMP. It has been used to treat cancer pain when cancer has spread to the bone. Once injected into a vein, it distributes throughout the body and localizes in areas' where cancer has invaded the bone, allowing the beta particles (electrons) to destroy the nearby cancer cells. It is also commonly used in lung cancer, prostate cancer, breast cancer, and osteosarcoma. Yttrium-90 has been used in the treatment of various cancers including lymphoma, leukemia, ovarian, colorectal, pancreatic, and bone cancers, and in treatment of rheumatoid arthritis by radionuclide synovectomy.

Although an attempt is made to provide an exhaustive list, it is well-known to nuclear medicine specialists that radioisotopes may be produced using a generator system like Mo—Tc or Sn/In systems, a thermal neutron reactor, a cyclotron, or fission produced. Accordingly, any radioisotopes with functional equivalents to those listed are intended to be encompassed wherever appropriate within the scope of the present invention.

Glass Preparation

The microparticles of the present invention may be prepared from a homogenous mixture of powders (i.e., the batch) that is melted to form the desired glass composition. The exact chemical compounds or raw materials used for the batch is not critical so long as they provide the necessary oxides in the correct proportion for the melt composition being prepared. For instance, for making a strontium borate glass, then strontium, borate, and/or soda, powders may be used as some the batch raw materials. The purity of each raw material is preferably greater than 99.9%. After either dry or wet mixing of the powders to achieve a homogeneous mixture, the mixture may be placed in a platinum crucible for melting. High purity alumina crucibles can also be used if at least small amounts of alumina can be tolerated in the glass being made. The crucibles containing the powdered batch are then placed in an electric furnace which is heated 1000° C. to 1600° C. depending upon the composition. In this temperature range, the batch melts to form a liquid which is stirred several times to improve its chemical homogeneity. The melt should remain at 1000° C. to 1600° C. till all solid material in the batch is totally dissolved, usually 4-10 hours being sufficient. Significantly, by not incorporating the radioisotope into the melt, no radioisotope can be vaporized, thus avoiding a radiation hazard.

Another advantage of the invention is the ability to use radioisotopes that have a shorter half-life. For example, Tc-99m (Technetium-99m) cannot be made part of the glass, i.e. the half-life may often be too short to be useful when it is incorporated as part of certain homogeneous glass-radioisotope compositions. Additionally, the ability to use radioisotopes that would otherwise be destroyed or degrade by the glass-melt process. For example, trying to incorporate Technetium or Rhodium into a melt would vaporize the Technetium or Rhodium.

When melting and stirring is complete, the crucible is removed from the furnace and the melt is quickly quenched to a glass by pouring the melt onto a cold steel plate or into clean, distilled water. This procedure breaks the glass into fragments, which aids and simplifies crushing the glass to a fine powder. The powder is then sized and spheroidized for use.

Spheroidizing

To obtain spheroid microparticles having a diameter in the desired range of micrometers, the glass is processed using varying techniques such as grinding and passing through mesh sieves of the desired size, where the glass particles may be formed into spheroids by passing the sized particles through a gas/oxygen flame where they are melted and a spherical liquid droplet is formed by surface tension. A vibratory feeder located above the gas/oxygen burner slowly vibrates the powder into a vertical tube that guides the falling powder into the flame at a typical rate of 5-25 gm/hr. The flame is directed into a metal container which catches the spheroidized particles as they are expelled from the flame. The droplets are rapidly cooled before they touch any solid object so that, their spherical shape is retained in the solid product.

After spheroidization, the glass spheres are preferably collected and rescreened based upon size. As a non-limiting example, when the microparticles are intended to be used in the treatment of liver cancer, the fraction less than 30 and greater than 20 micrometers in diameter is recovered since this is a desirable size for use in the human liver. After screening, the −30/+20 microparticles are examined with an optical microscope and are then washed with a weak acid (HCl, for example), filtered, and washed several times with reagent grade acetone. The washed spheres are then heated in a furnace in air to 500-600° C. for 2-6 hours to destroy any organic material.

The final step is to examine a representative sample spheres in a scanning electron microscope to evaluate the size range and shape of the spheres. The quantity of undersize spheres (less than 10 micrometers in diameter) is determined along with the concentration of non-spherical particles. The composition of the spheres can be checked by energy dispersive x-ray analysis to confirm that the composition is correct and that there is an absence of chemical contamination.

The glass microparticles are then ready for phosphate conversion, bonding with radionuclide, and subsequent administration to the patient.

In accordance with the present invention, the above processing steps are merely exemplary and do not in any way limit the present invention. Similarly, the present invention is not limited to glass microparticles having a size described above; the size of the microparticles of the present invention may be varied according to the application.

Types of Cancers

The microparticles of the present invention may be used in a variety of clinical situations, including but not limited to: selective internal radiation therapy for tumors of areas that have favorable vasculature, including the liver, spleen, brain, kidney, head & neck, uterine, and prostate. The microparticles may also be used for imaging, including a Liver/Spleen Scan—for tumors, cysts or hepatocellular disease; a Brain Scan—for tumors, trauma, or dementia; a Tumor Scan for malignant tumors or metastatic disease of the Kidney, Head & Neck, Uterine/Gynecological; and any Scan or Therapy having favorable vasculature for this approach.

One radionuclide imaging technique contemplated as within the scope of the invention is single photon emission computed tomography (SPECT).

Since most organs, besides the liver, have only one blood vessel that feeds it, administration may be performed by delivery to that main feeder artery and allowing the microparticles to lodge in the capillary bed since they are too large to move through the capillary. The liver may require a specialized delivery regimen. In another embodiment, the vessel that feeds the tumor may be identified, and this artery is used to deliver the microparticles.

As various changes could be made in the above methods and products, without departing from the scope of the invention, it is intended that all matter contained in the above description or shown in any accompanying drawings shall be interpreted as illustrative and not in a limiting sense. Any references recited herein are incorporated herein in their entirety, particularly as they relate to teaching the level of ordinary skill in this art and for any disclosure necessary for the commoner understanding of the subject matter of the claimed invention. It will be clear to a person of ordinary skill in the art that the above embodiments may be altered or that insubstantial changes may be made without departing from the scope of the invention. Accordingly, the scope of the invention is determined by the scope of the following claims and their equitable equivalents.

The invention claimed is:

1. A process for the preparation of a strontium phosphate radiomicroparticle comprising
   (i) reacting a strontium-containing borate glass microparticle with a phosphate solution such as to at least partially convert the strontium-containing borate glass of the microparticle to strontium phosphate; and
   (ii) bonding at least one radioisotope suitable for radioimaging and/or radiotherapy to said microparticle to form said radiomicroparticle by exposing the strontium phosphate to the at least one radioisotope.

2. The process of claim 1, wherein the strontium-containing borate-glass microparticle is a microsphere.

3. The process of claim 1, wherein the strontium-containing borate glass microparticle has a diameter of about 5 μm to about 1000 μm.

4. The process of claim 1, wherein the strontium phosphate microparticle has a surface area of between about 90 to about 200 square meters per gram.

5. The process of claim 1, wherein the strontium phosphate is crystalline.

6. The process of claim 1 wherein the strontium-containing borate glass microparticle is substantially completely converted to strontium phosphate.

7. The process of claim 1 wherein the strontium-containing borate glass microparticle is substantially completely converted to crystaline strontium phosphate.

8. The process of claim 1 wherein the at least one radioisotope is a therapeutic beta-emitting radioisotope.

9. The process of claim 1, wherein the at least one radioisotope is a diagnostic gamma-emitting radioisotope.

10. The process of claim 1, wherein the at least one radioisotope is a combination of a one or more gamma emitting radioisotope and one or more beta emitting radio isotopes.

11. The process of claim 1, wherein the at least one radioisotope is selected from the group consisting of Actinium-225, Antimony-127, Arsenic-74, Barium-140, Bismuth-210, Californium-246, Calcium-46, Calcium-47, Carbon-11, Carbon-14, Cesium-131, Cesium-137, Chromium-51, Cobalt-57, Cobalt-58, Cobalt-60, Dysprosium-165, Erbium-169, Fluorine-18, Gallium-67, Gallium-68, Gold-198, Holmium-166, Hydrogen-3, Indium-111 Indium-113m, Iodine-123, Iodine-125, Iodine-131, Iridium-192, Iron-59, Iron-82, Krypton-81m, Lanthanum-140, Lutetium-177, Molybdenum-99, Nitrogen-13, Oxygen-15, Paladium-103, Phosphorus-32, Radon-222, Radium-224, Rhenium-186, Rhenium-188, Rhubidium-82, Samarium-153, Selenium-75, Sodium-22, Sodium-24, Strontium-89, Technetium-99m, Thallium-201, Xenon-127, Xenon-133, Yttrium-90, and combinations thereof.

12. The process of claim 1, wherein the at least one radioisotope is selected from the group consisting of Technetium-99m, Indium-111, Lutetium-177, Sarnarium-153, Yttrium-90, Holmium-166, Gallium-68 and Fluorine-18.

13. The process of claim 1, wherein the at least one radioisotope is a combination of radioisotopes selected from the group consisting of Y-90/In-111 Y-90/Tc-99rn, P-32/In-111, P-32/Tc-99m, Ho-166/In-111, Ho-166/Tc-99m, Sm-153/In-111, and Sm-153/Tc-99m.

14. A process for the preparation of a strontium phosphate radiomicroparticle comprising
   (i) reacting a strontium-containing borate glass microparticle with a phosphate solution such as to at least partially convert the strontium-containing borate glass of the microparticle to a crystalline strontium phosphate microparticle having a surface area between about 90 and about 200 square meters per gram; and
   (ii) bonding at least one radioisotope suitable for radioimaging and/or radiotherapy to said radiomicroparticle by exposing the strontium phosphate to the at least one radioisotope.

15. The process of claim 12 wherein the crystalline strontium phosphate microparticle is a microsphere having a diameter between 5 and 200 μms.

16. The process of claim 1 wherein the bonding comprises mixing the microparticle in with the at least one radioisotope.

17. The process of claim 1 wherein the bonding comprises mixing the microparticle in a solution containing the at least one radioisotope.

* * * * *